United States Patent [19]

Timperley

[11] Patent Number: 5,788,704

[45] Date of Patent: Aug. 4, 1998

[54] APPARATUS AND METHOD FOR IMPLANTING A PROTHESIS

[75] Inventor: Andrew J. Timperley, Bradsford, England

[73] Assignee: Howmedica International Inc., Shannon, Ireland

[21] Appl. No.: 808,764

[22] Filed: Mar. 3, 1997

Related U.S. Application Data

[63] Continuation of Ser. No. 536,289, Sep. 29, 1995.

[30] Foreign Application Priority Data

Oct. 5, 1994 [GB] United Kingdom ............... 9420050

[51] Int. Cl.⁶ ............................................. A61B 17/56
[52] U.S. Cl. ..................... 606/95; 606/86; 606/92; 606/93; 606/94; 623/23
[58] Field of Search ..................... 606/85, 86, 92, 606/93, 94, 95, 99; 623/23

[56] References Cited

U.S. PATENT DOCUMENTS 5,100,407  3/1992  Conard et al. .................. 606/79
5,156,606  10/1992  Chin ............................... 606/92
5,192,283  3/1993  Ling et al. ....................... 606/93

Primary Examiner—Michael Buiz
Assistant Examiner—Daphna Shai
Attorney, Agent, or Firm—Peter C. Richardson; Lawrence C. Akers; Raymond W. Augustin

[57] ABSTRACT

An apparatus for performing prosthesis surgery has a phantom implant component. Elements are provided for holding said phantom component accurately and stationary relative to a cavity in a bone. The phantom component has a tapered insert portion, the dimensions of which are identical to the insert portion of an implant component which is to be fitted. A method of performing prosthesis surgery is included which uses the apparatus set forth above which includes preparing an opening in a bone with cement, inserting the insert portion of the phantom component, allowing the cement to at least partially set, removing the phantom component, inspecting the cement and then inserting the implant component with the identical insert portion dimensions.

8 Claims, 5 Drawing Sheets

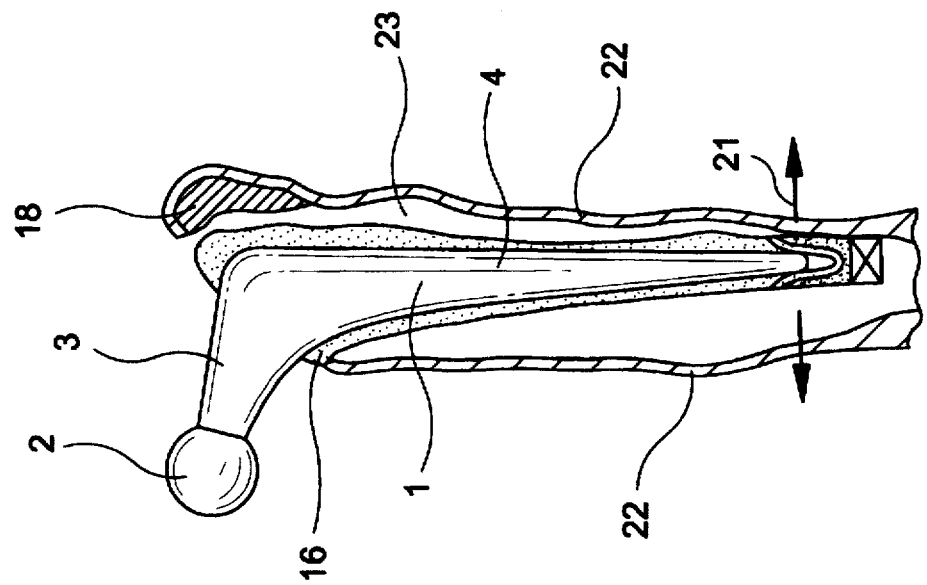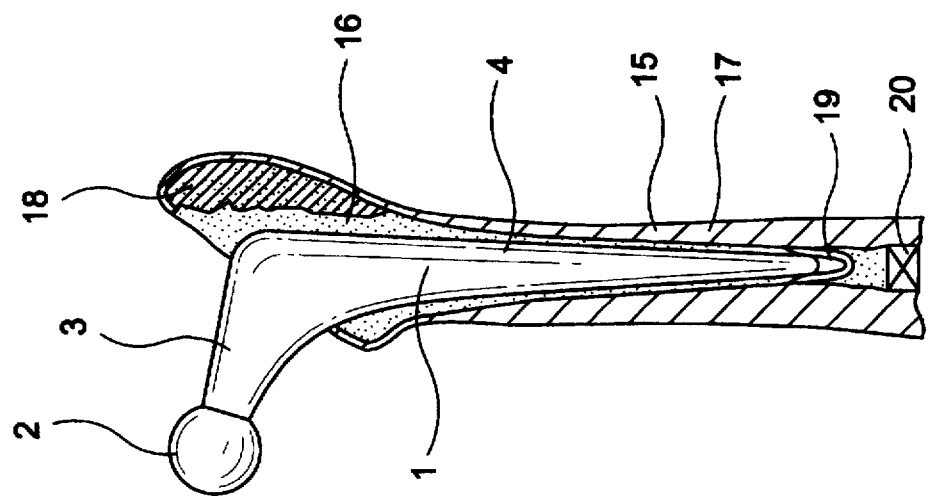

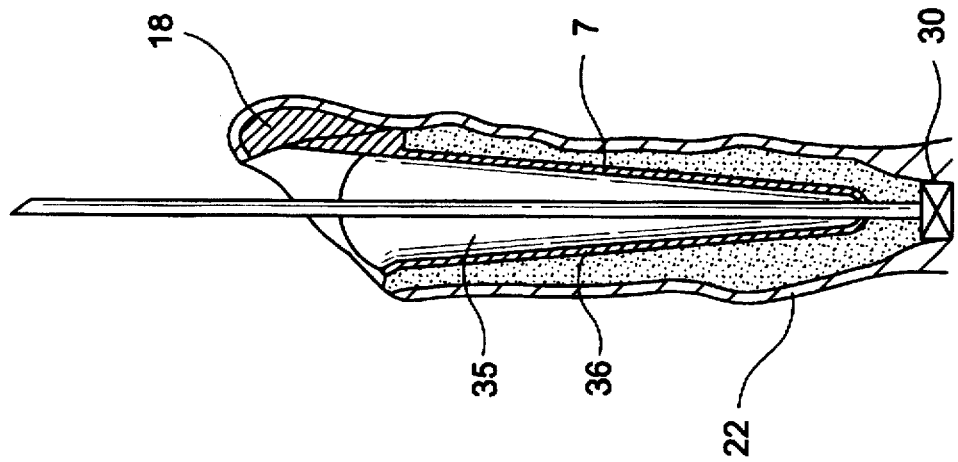
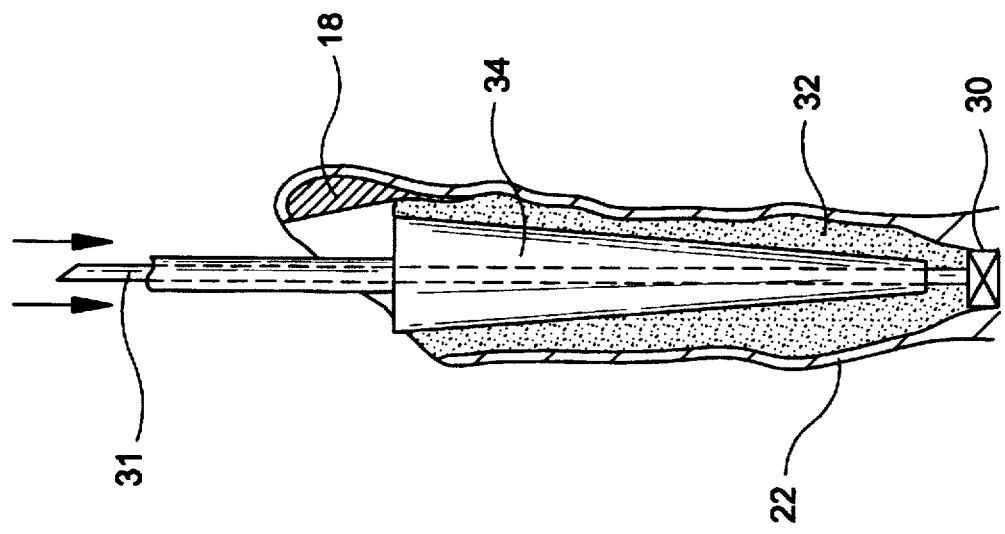

APPARATUS AND METHOD FOR IMPLANTING A PROTHESIS

This is a continuation, of application Ser. No. 08/536,289, filed on Sept. 29, 1995, which is still pending.

BACKGROUND OF THE INVENTION

1. Field of the Invention

The present invention relates to apparatus and a method for implanting a prosthesis, for example a total hip prosthesis. Particularly it relates to a method using bone cement to hold the prosthesis in place.

2. Description of the Prior Art

The problem with present prosthesis implanting techniques is the difficulty of guaranteeing the position and thickness of an adequate cement mantle around a cemented implant and the present invention is intended to provide means for overcoming this difficulty.

SUMMARY OF THE INVENTION

According to the present invention apparatus for performing prosthesis surgery comprises a phantom implant component, a means for holding the phantom component accurately and stationary relative to a cavity in a bone. The phantom component having a tapered insert portion, the dimensions of which are identical to the insert portion of an implant component which is to be fitted in the cavity.

If desired a second implant component can be provided the insert portion of which has dimensions which are smaller than the insert portion of said phantom component or the second implant component can be provided in place of the first.

The invention also includes a method of performing prosthesis surgery using the apparatus set forth above which includes preparing an opening in a bone including placing cement therein, inserting said insert portion of the phantom component, allowing the cement to at least partially set, removing said phantom component, inspecting the cement and then inserting the implant component with the identical insert portion dimensions.

Alternatively, if a second implant component is provided of smaller dimensions than the first then more cement can be packed into the cavity and the second implant component with the smaller insert portion inserted.

The various components can be provided as a kit of parts which can be used as desired in the circumstances of the operation.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 1 is a diagrammatic cross-section showing the installation of a total hip prosthesis of known kind in a femur; and, FIGS. 2 to 10 are part cross-sectional side elevations showing how a hip prosthesis of the kind shown in FIG. 1 can come lose and be replaced by the method according to the present invention.

DESCRIPTION OF THE PREFERRED EMBODIMENT

Figure 3:
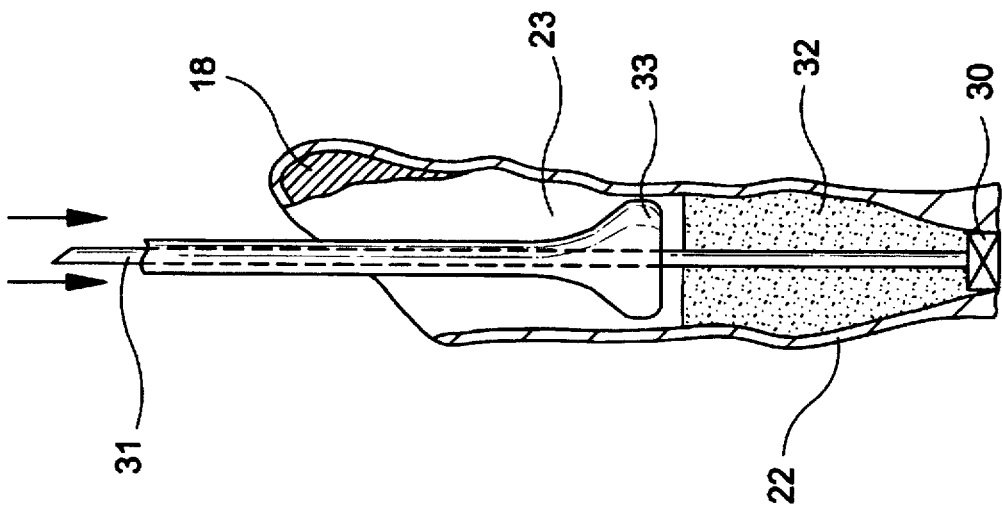
Figure 4:
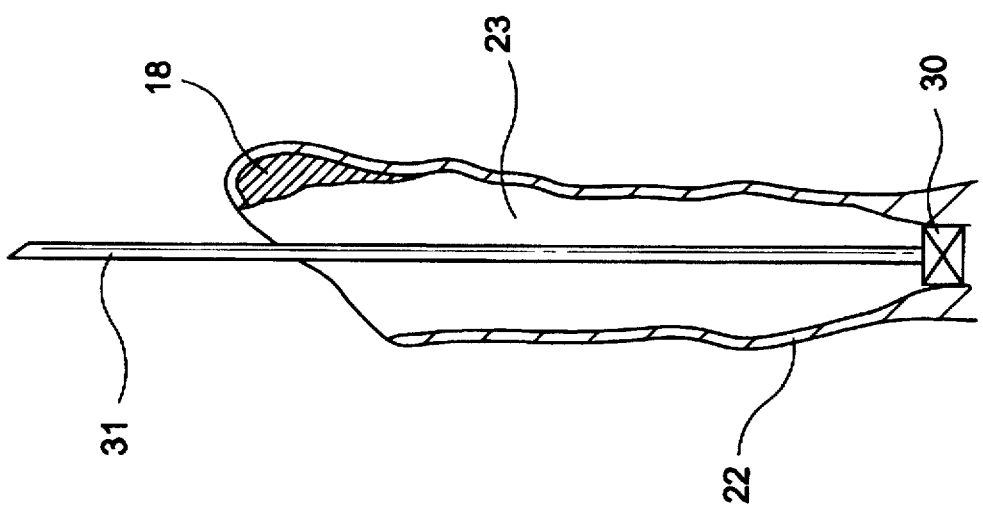

FIG. 1 shows an idealized primary hip intramedullary femoral prosthesis 1 of the straight tapering collarless polished design known as an "EXETER" hip located in a femur 15. The prosthesis has a head 2, neck 3 and stem 4 and is held in place by bone cement indicated by reference numeral 16. The cortical bone 17 of the femur 15 retains some cancellous bone 18. The stem 4 is centralized in the canal by a centralizer 19 of known type and the canal is plugged by a known bone plug 20.

FIG. 2 illustrates what can happen when an implant as shown in FIG. 1 fails. The stem 4 together with the cement 16 break away from the bone and a pendulum effect is produced as shown by arrows 21. The causes severe damage within the bone so that all that is left is a thin cortex 22. A space 23 is created which becomes filled by fluids and fibrous tissues.

U.S. Pat. No. 5,192,283 shows an implant and a method by which the damaged joint can be repaired and this method will now be described further showing how it can be used in the present invention. The revision procedure commences as shown in FIG. 3 by removing the implant complete with cement and the fibrous tissue by first fitting a bone plug 30 and guide wire 31. Bone chips 32 are now added and compressed using an impactor or ram 33. The bone chips are built up layer by layer in the manner described in U.S. Pat. No. 5,192,283 and a stem phantom 34 is then introduced as shown in FIG. 5 to readily compress the bone chips and form a cavity 35 which is most clearly shown in FIG. 6.

A lining 36 of cement is now applied to the cavity 35 and this may be pressurized if desired. A cannulated phantom 50 is now introduced into the opening 35, the insert portion 51 having dimensions which are identical with those of a prothesis which is intended to be fitted. The guide wire 31 provides means for accurately locating the phantom 50 in place. Pressurization may again be performed and the cement is allowed to cure or at least partially set. It is during this stage that the phantom must be held accurately and stationery relative to the cavity and this is achieved by the guide wire 31 which passes through the cannulation in the phantom. Once the cement is cured or in a suitable state the phantom 50 is withdrawn from the cavity. To allow this the phantom 50 will generally have a polished surface or alternatively be coated with a material which does not adhere to the curing bone cement and it cannot have any features which would make it difficult to remove it from the cement. Where the guide wire system is used the guide wire is now unthreaded from the intramedullary plug 30 and withdrawn. The surgeon may now physically examine the cement cavity formed identifying whether there are specific areas where the cement mantle is incomplete or identifying other defects.

Figure 8:
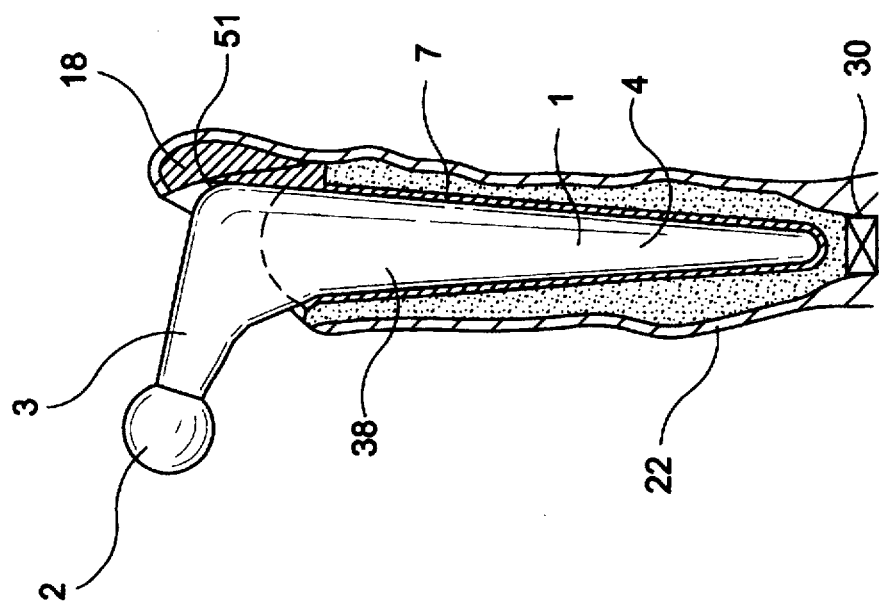
Figure 7:
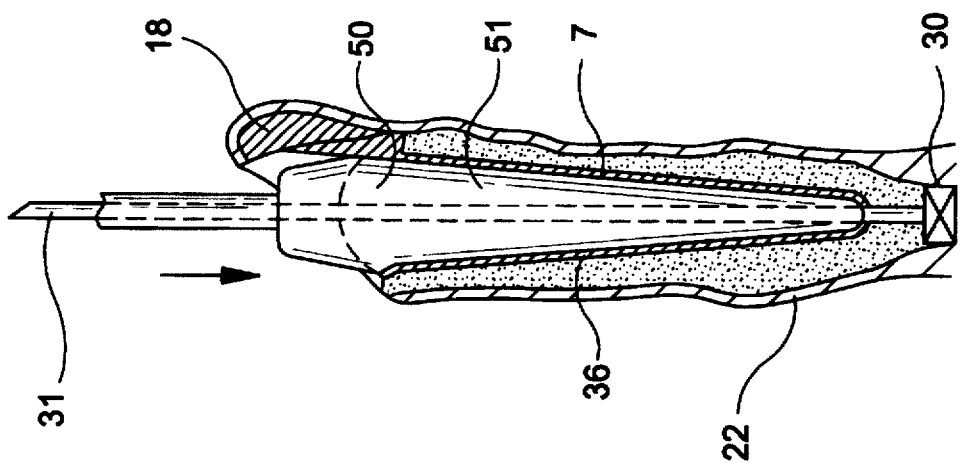
Figure 10:
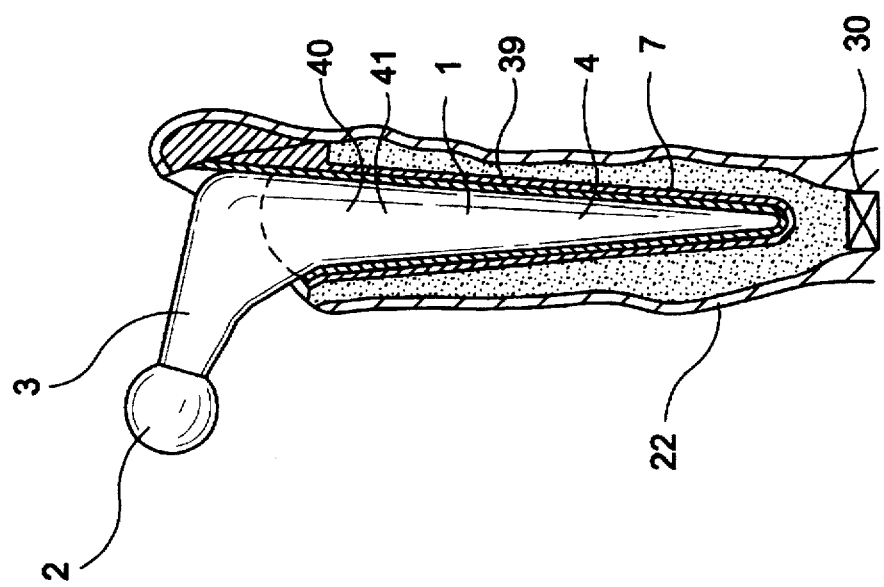
Figure 9:
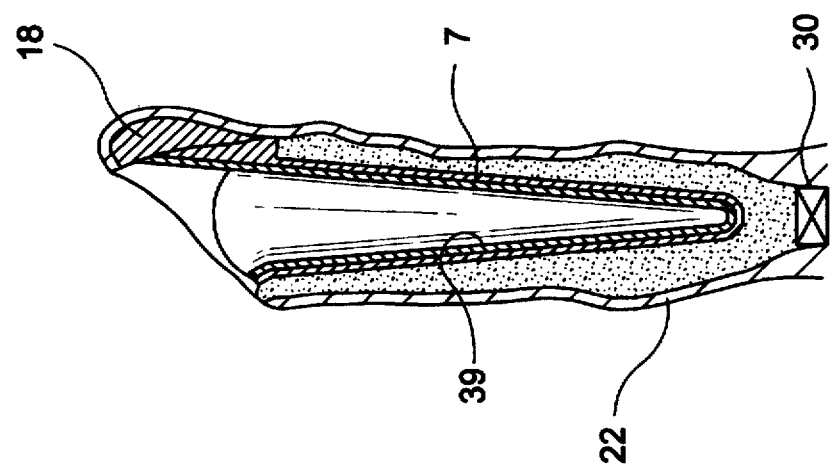

The surgeon now has two choices. If the mantle 36 as formed is entirely adequate he may use this for the fixation of the eventual implant component which is identified by reference numeral 38 in FIG. 8.

If the cement mantle has defects however a further quantity of cement 39 is introduced into the cement cavity already formed, so as to fill any defects, and then an alternative prosthesis is introduced. This prosthesis 40 has an insert portion 41 which is of smaller size than the insert portion 51 of the phantom 50. Thus this is used as the final implantation.

The use of this technique is dependent upon the form of an ultimate implant to be cemented into the cavity, since the phantom may not have any retrograde features that result in it being locked into the cement.

The stem geometry must allow an appropriate mechanism for the transmission of the load between the stem and the cement mantle so formed and an ideal hip stem for the use of this technique is the EXETER hip stem. This type of stem incorporates a double tapered and polished stem form which effectively engages the cement mantle causing principally compressive transmission of load from the stem to the cement and thereby to the bone.

This selection is important if the surgeon chooses to use the original cement mantle formed by the phantom 50 with the definitive implanted stem. Inevitably manufacturing variations will result in a marginal mismatch between the mantle and the definitive stem. The use of the double tapered stem which allow tapered reengagement to occur with the relative compliant and visco-elastic cement at body temperature results in the effective taper load transmission despite the manufacturing differences.

With existing techniques there can be inappropriate positioning of an implant within the cavity in the bone and they do not result in a uniform control thickness of cement mantle which would give a better mechanical performance of the cement. This is a particular advantage of the new method of insertion.

This method can also be used with a cannulated system of broaches for shaping the opening. They can be used to form a known cavity shape over and above the nominal size of the implant and further guarantee the mantle geometry.

A system of depth indicators can be used for example as shown in the technique described in U.S. Pat. No. 5,192,283 and the depth indication system could also be used to position the phantom insert within the cavity formed by such broaches.

Thus, the new method involves the use of an instrument, the phantom insert, which more or less guarantees the provision of an adequate and complete cement mantle of predetermined thickness around a cemented implant.

While several examples of the present invention have been described, it is obvious that many changes and modifications may be made thereunto, without departing from the spirit and scope of the invention.

I claim:

1. A method of performing prosthesis surgery using a phantom implant component, a holding element for holding said phantom implant component accurately and stationary relative to a cavity in a bone, said phantom component having a tapered insert portion the dimensions of which are identical to or larger than the insert portion of an implant component which is to be fitted in the cavity comprising;

the steps in the following order:

filling a cavity in a bone with cement;

inserting said insert portion of the phantom component, said insert portion having a surface which resists adhesion to bone cement;

allowing the cement to at least partially set;

removing said phantom component to form a cavity in said bone cement;

inspecting the cement of said cavity; and inserting the implant component with the identical or smaller insert portion dimensions.

2. The method of claim 1 wherein said phantom component has a tapered insert portion the dimensions of which are identical to or larger than the insert portion of an implant component which is to be fitted in the cavity.

3. The method of claim 1 wherein said implant component has a tapered insert portion the dimensions of which are identical with those of the insert portion of said phantom component.

4. The method of claim 1 wherein said implant component which is to be fitted and which has a tapered insert portion the dimensions of which are smaller than the insert portion of said phantom component.

5. The method of claim 1 wherein said phantom component is connected and includes a means for holding said phantom component accurately and stationary using a guide wire.

6. The method of claim 1 wherein said phantom component has a polished finish or is coated with a material which will not adhere to curing bone cement.

7. The method of claim 1 wherein said implant component is for a total hip prosthesis.

8. A method of implanting an orthopedic prosthesis having a stem portion for insertion into a bone cavity including the steps in the following order:

preparing said cavity;

filling said cavity with cement;

inserting a tapered insert portion of a phantom component having the same size and shape of the stem portion of said implant, said insert portion having a surface which resists adhesion to bone cement;

allowing the cement to at least partially set;

removing said phantom component to form a cavity in said cement;

inspecting the cement cavity formed by said phantom component; and inserting the implant component into said cavity.

* * * * *